US009044634B2

United States Patent
Hjelt et al.

(10) Patent No.: US 9,044,634 B2
(45) Date of Patent: Jun. 2, 2015

(54) DYNAMICALLY CONFIGURABLE BALANCING BOARD

(71) Applicants: Kari Hjelt, Espoo (FI); Seppo Keronen, Balmain (AU)

(72) Inventors: Kari Hjelt, Espoo (FI); Seppo Keronen, Balmain (AU)

(*) Notice: Subject to any disclaimer, the term of this patent is extended or adjusted under 35 U.S.C. 154(b) by 158 days.

(21) Appl. No.: 13/787,509

(22) Filed: Mar. 6, 2013

(65) Prior Publication Data
US 2013/0237395 A1 Sep. 12, 2013

(30) Foreign Application Priority Data
Mar. 9, 2012 (GB) .................................. 1204183.6

(51) Int. Cl.
A63B 22/14 (2006.01)
A63B 71/00 (2006.01)
A63B 26/00 (2006.01)
A63B 22/18 (2006.01)
A63B 21/008 (2006.01)
(Continued)

(52) U.S. Cl.
CPC ............... *A63B 26/003* (2013.01); *A63B 22/18* (2013.01); *A63B 21/0085* (2013.01); A63B 2071/0625 (2013.01); A63B 2071/0677 (2013.01); A63B 2071/068 (2013.01); A63B 2220/10 (2013.01); A63B 2220/18 (2013.01); A63B 2220/24 (2013.01); A63B 2220/40 (2013.01); A63B 2220/51 (2013.01); A63B 2220/803 (2013.01); A63B 2220/806 (2013.01); A63B 2220/808 (2013.01); A63B 2225/62 (2013.01); A63B 2230/062 (2013.01); *A63B 21/00196* (2013.01); *A63B 24/0087* (2013.01); A63B 2024/009 (2013.01); A63B 2024/0093 (2013.01); A63B 2071/0072 (2013.01); A63B 2071/0081 (2013.01); A63B 2071/0683 (2013.01); A63B 2220/836 (2013.01); A63B 2225/20 (2013.01); A63B 2225/50 (2013.01); A63B 2230/00 (2013.01); A63B 69/0053 (2013.01); *A63B 71/0622* (2013.01); *A63B 24/0084* (2013.01); *G06F 19/3481* (2013.01); *H04M 1/7253* (2013.01); *H04M 1/72558* (2013.01); A63B 2022/185 (2013.01); A63B 2024/0068 (2013.01); A63B 2207/02 (2013.01); H04M 2250/12 (2013.01); G08C 2201/93 (2013.01); *G08C 17/02* (2013.01)

(58) Field of Classification Search
USPC ...................................... 482/146, 147, 142, 8
See application file for complete search history.

(56) References Cited

U.S. PATENT DOCUMENTS

5,897,474 A * 4/1999 Romero .......................... 482/146
6,575,885 B1 * 6/2003 Weck et al. ................... 482/147
(Continued)

*Primary Examiner* — Loan H Thanh
*Assistant Examiner* — Megan Anderson
(74) *Attorney, Agent, or Firm* — MP Patents, LLC (57) ABSTRACT

A balancing board comprises a first surface for receiving one or more feet of a user when the balancing board is in operation. The balancing board includes a second surface of one or more outwardly curved forms for engaging with a floor surface, wherein the second surface enables variations in an orientation and movement of the balancing board relative to the floor surface. The balancing board further includes a signal receiving arrangement for receiving sensor signals indicative of one or more user reactions when operating the balancing board in reaction to the variations in the orientation and movement of the balancing board. The user is supported upon the first surface of the balancing board; and a processor operable to receive signals from the first set of sensors. The processor is operable to activate one or more modes of operation of the balancing board based on the received signals.

19 Claims, 5 Drawing Sheets (51) Int. Cl.
*A63B 21/00* (2006.01)
*A63B 24/00* (2006.01)
*H04M 1/725* (2006.01)
*G08C 17/02* (2006.01)
*A63B 71/06* (2006.01)
*A63B 69/00* (2006.01)
*G06F 19/00* (2011.01)

(56) References Cited

U.S. PATENT DOCUMENTS

| | | | |
|---|---|---|---|
| 8,234,798 B2* | 8/2012 | DiBenedetto et al. | 36/132 |
| 8,235,871 B2* | 8/2012 | Mikan et al. | 482/9 |
| 2004/0198573 A1* | 10/2004 | Brydson et al. | 482/146 |
| 2007/0270296 A1* | 11/2007 | Caldicott | 482/146 |

* cited by examiner

DYNAMICALLY CONFIGURABLE BALANCING BOARD

BACKGROUND

The invention generally relates to an exercise or recreational equipment. More specifically, the invention relates to a dynamically configurable balancing board.

A balancing board is equipment that is used for the purpose of recreation and exercise. The balancing board includes a platform on which a user can stand and a fulcrum, for example, a spherical cup, that engages with the ground. A user stands on the platform of the balancing board and tries to maintain his/her balance such that the platform of the balancing board does not touch the ground. Conventional balancing boards that are currently used are not versatile. Moreover, they are not efficient in providing an effective exercise regime to a user. There is therefore a need for a balancing board that is more versatile and efficient.

SUMMARY

In an embodiment, a balancing board is provided including a first surface for receiving one or more feet of a user when said balancing board is in operation, a second surface of one or more outwardly curved forms for engaging with a floor surface when said balancing board is in operation and providing means for varying an orientation and movement of the balancing board relative to the floor surface, a signal receiving arrangement for receiving one or more sensor signals indicative of one or more user reactions when operating the balancing board in reaction to variations in the orientation and movement of the balancing board, and a processor operable to receive signals from a first set of sensors indicative of said one or more user reactions, wherein the processor is further operable to control means of changing a profile of the second surface.

BRIEF DESCRIPTION OF THE FIGURES

The accompanying figures, where like reference numerals refer to identical or functionally similar elements throughout the separate views, and which together with the detailed description below are incorporated in and form part of the specification, serve to further illustrate various embodiments and to explain various principles and advantages.

DETAILED DESCRIPTION

Before describing embodiments in detail, it should be observed that the embodiments reside primarily in combinations of method steps and system components related to a dynamically configurable balancing board. Accordingly, the system components and method steps have been represented where appropriate by conventional symbols in the drawings, showing only those specific details that are pertinent to understanding the embodiments so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. A set may include zero or more elements.

Various embodiments provide a balancing board comprising a first surface for receiving one or more feet of a user when the balancing board is in operation, characterized by: the balancing board including a second surface of one or more outwardly curved forms for engaging with a floor surface when the balancing board is in operation, wherein the second surface enables variations in an orientation and movement of the balancing board relative to the floor surface; the balancing board including a signal receiving arrangement for receiving one or more sensor signals indicative of one or more user reactions when operating the balancing board in reaction to the variations in the orientation and movement of the balancing board, wherein the user is supported upon the first surface of the balancing board; and a processor operable to receive signals from the first set of sensors indicative of the one or more user reactions, wherein the processor is further operable to activate one or more modes of operation of the balancing board based on the received signals.

Figure 1:
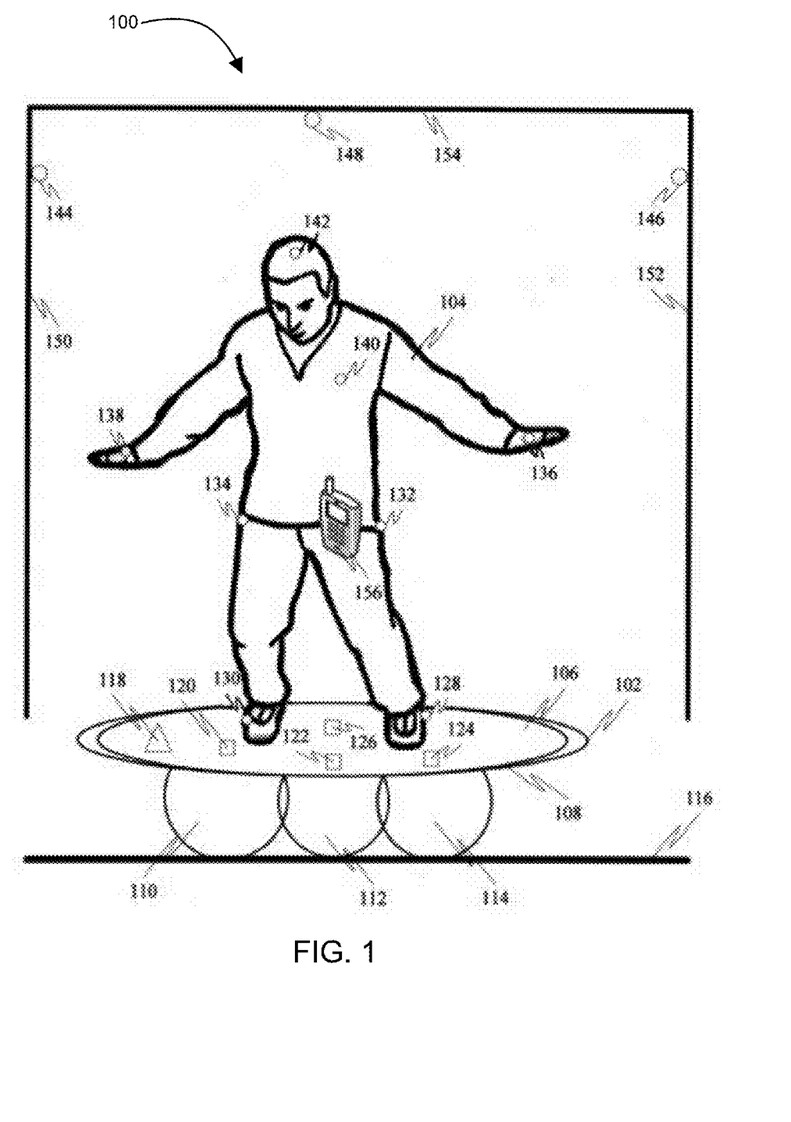
FIG. 1 illustrates a side view of a balancing board in accordance with an example embodiment.

FIG. 1 is a side view 100 of an example balancing board 102 in use by a user 104, in accordance with an embodiment. The balancing board 102 is used by user 104 for exercising or recreation by maintaining his/her balance while standing on top of balancing board 102. To support weight of user 104, the balancing board 102 is fabricated from one or more materials, for example, wood, plastics material, composite fiber, metal, toughened glass or any combination thereof. The balancing board 102 may be circular in shape. Alternatively, the balancing board 102 may have any polygonal shape on which user 104 can stand.

The balancing board 102 includes a first surface 106 for receiving one or more feet of the user 104 when he/she is operating the balancing board 102. In other words, the user 104 stands on the first surface 106 to operate the balancing board 106. In an embodiment, the first surface 106 may be a planar surface. Alternatively, the first surface 106 may be slightly concave or convex, or even provided with a peripheral outwardly projecting lip feature to assist the user 104 retain his/her one or more feet engaged onto the first surface 106. In both the cases, the first surface 106 may have an unsmooth texture to enable better foot traction for the user 104. For example, multiple small projections or indentations may be formed on the first surface 106 while molding it. By way of another example, rubber grip mats may be fixed onto the first surface 106.

In addition to the first surface 106, the balancing board 102 has a second surface 108 that includes one or more outwardly curved forms (for example, a curved form 110, a curved form 112, and a curved form 114). Each of the curved form 110, the curved form 112, and the curved form 114 may be equidistant from each other. Additionally, the curved forms 110, 112, and 114 may be equidistant from a substantially central axis of the balancing board 102, wherein the central axis is substantially orthogonal and central to the first surface 106. In other words, the curved forms 110, 112, and 114 may be equidistant either from the central axis of the balancing board 102 or from an axis offset from the central axis of the balancing board 102.

An outwardly curved form may be made up of an inflatable material, for example, rubber, fabric, wire, polyvinyl chloride, or any combination thereof. Alternatively, the outwardly curved form may be solid that is made up of one or more materials. Examples of the one or more materials may include but are not limited to rubber, plastics material, wood, glass, and metal. Each of the one or more outwardly curved forms may be a spherical cap, such that the flat portion of the spherical cap is attached to second surface 108 and the spherical portion engages with a floor surface 116 onto which balancing board 102 is placed.

By engaging with the floor surface 116, the one or more outwardly curved forms enable the user 104 to operate the balancing board 102. The one or more curved forms act as a fulcrum to the balancing board 102 and thus help the second surface 108 to enable variation in an orientation and movement of the balancing board 102 relative to the floor surface 116. The orientation and movement of the balancing board 102 may be varied by sliding, rotating, tilting, or rolling it. For example, in a natural or stable position of the balancing board 102, the first surface 106 is substantially parallel to the floor surface 116. However, variation in orientation and movement of the balancing board 102 may change the angle of the first surface 106 with respect to the floor surface 116.

Moreover, variation is orientation, movement, and acceleration of the balancing board 102 is dependent on one or more modes of operations selected for the balancing board 102. The one or more modes of operations are activated by a processor 118 included within balancing board 102. The one or more modes of operations further include a plurality of balancing board levels, namely difficulty levels as experienced by the user 104. Each of the balancing board levels has a predefined combination of orientation, movement, and acceleration of the balancing board 102. For example, the balancing board 102 may have four levels, i.e., beginner, easy, medium, and tough. For each of these levels, there would be a respective combination of orientation, movement, and acceleration of the balancing board 102. The beginner level may have the least variations in orientation, movement, and acceleration possible for the balancing board 102, and the tough level may have the most extreme variations in orientation, movement, and acceleration possible for the balancing board 102, such that, the user 104 would have to be an expert to maintain his/her balance on the balancing board 102.

To activate a mode of operation of the balancing board 102 and thus enable these variations in the balancing board 102, the processor 118 communicates with one or more actuators (for example, an actuator 120, an actuator 122, an actuator 124, and an actuator 126) that are provided in the balancing board 102 at multiple locations therein. Examples of actuators for use in the balancing board 102 may include but are not limited to motors, magnetic solenoids, motors coupled to eccentric weights and so forth. Optionally, the balancing board 102 is capable of being configured to switch randomly between its plurality of modes of operations, with a sound signal and/light signal emitted from the balancing board 102 when its mode of operation is randomly altered; such a manner of operation provides additional user interest and excitement.

Based on a mode of operation selected by the processor 118, the one or more actuators inflate or deflate a volume of gas in the one or more outwardly curved forms to modify orientation, movement, and acceleration of the balancing board 102. The one or more outwardly curved forms are defined at least in part by the volume of gas under pressure filled by the one or more actuators. In other word, the shape of the one or more outwardly forms is modified based on the volume of gas pumped inside them by the one or more actuators. For example, each of the curved forms 110, 112, and 114 may take the shape of a spherical cap when fully inflated.

As an example of activation of a mode of operation of the balancing board 102, the actuator 120 may inflate or deflate the curved form 110, the actuator 122 may inflate or deflate the curved form 112, and the actuator 124 may inflate or deflate the curved form 114. Based on the mode of operation activated by the processor 118, the curved form 110, the curved form 112, and the curved form 114 may be selectively or alternatively inflated or deflated by their respective actuator so as to change the orientation, movement, and acceleration of the balancing board 102. In one scenario, deflation of the curved form 112 may result in tilting of the balancing board 102 towards the floor surface 106 on the side where the curved form 112 is located. The user 104 may then have to counterbalance the balancing board 102 by exerting more pressure on one or more portions of the first surface 106 that are substantially above the location of the curved forms 110 and 114. In another scenario, the curved form 112 may be inflated more than the curved forms 110 and 114, thereby tilting the balancing board 102 towards the floor surface 106 on the side where the curved forms 110 and 114 are located. The user 104 may then have to counterbalance the balancing board 102 by exerting more pressure on one or more portions of the first surface 106, which are substantially above the location of curved form 112.

In another embodiment, when the one or more outwardly curved forms are solid, the one or more actuators may selectively retract or extend the one or more outwardly curved forms to enable a mode of operation activated by the processor 118. In this case, each of the one or more actuators may include a piston arrangement that controls extending and retracting of an associated curved form. For example, the actuator 120 may retract or extend the curved form 110, the actuator 122 may retract or extend the curved form 112, and the actuator 124 may retract or extend the curved form 114. Based on the mode of operation activated by the processor 118, the curved form 110, the curved form 112, and the curved form 114 may be selectively or alternatively retracted or extended by their respective actuators so as to change the orientation, movement, and acceleration of the balancing board 102. In one scenario, retraction of the curved form 110 may result in tilting of the balancing board 102 towards the floor surface 106 on the side where the curved form 110 is located. The user 104 may then have to counterbalance the balancing board 102 by exerting more pressure on one or more portions of the first surface 106, which are above the location of the curved surfaces 112 and 114.

One of the one or more actuators may also create vibrations in the balancing board 102 based on a mode of operation activated. For example, the actuator 126 may create vibrations in the balancing board 102. The actuator 126 may, for example, be an electric motor with an unbalanced mass on its driveshaft. In an embodiment, the actuator 126 may rotate the first surface 106 independently about a substantially central axis of the balancing board 102. In other words, the first surface 106 may be rotated about the central axis of the balancing board 102 or about an axis offset from the central axis of the balancing board 102. The first surface 106 and the balancing board 102 may have a common central axis.

Thus, each balancing board level may also include rotation of the first surface 106 in addition to variation in orientation, movement, and acceleration of the balancing board 102. As a result, the user 104 will also have to counter or manage the rotary action of the first surface 106 while maintaining his/her balance. For example, the speed of rotation of the first surface 106 may be increased with increase in balancing board level. By way of another example, the first surface 106 may be rotated in bursts. The first surface 106 may also be alternately rotated in clockwise and anticlockwise direction.

To maintain his/her balance on the balancing board 102 when it is in operation, the user 104 has to counter the variations created in orientation, movement, and acceleration of the balancing board 102. Thus, body of the user 104 reacts to these variations in the balancing board 104 in various ways. To sense and capture the user 104's reaction, the balancing board 102 includes a first set of sensors (for example, sensors 128, 130, 132, 134, 136, 138, 140, 142, 144, and 146).

Examples of the first set of sensors may include but are not limited to one or more of an accelerometer, a gyroscope, a microphone, a pressure sensor, a force sensor, a camera, a depth sensor for gesture recognition, a biometric sensor, and a proximity sensor. The first set of sensors may at least in part be attached in operation to the body of the user 104. In other words, one or more sensors from the first set of sensors may be attached to a body of user 104 at different locations. For example, the sensors 128 and 130 are attached to feet of the user 104, the sensors 132 and 134 are attached to hips of the user 104, the sensors 136 and 138 are attached to hands of the user 104, the sensor 140 is attached near the heart of the user 104, and the sensor 142 is attached to a head of the user 104. Each of these sensors sense and capture reaction of the respective body parts of the user 104 in response to variation in orientation, movement, and acceleration of the balancing board 102. The sensors 128 and 130, for example, sense and capture corrective movement of user 104's feet to maintain his/her balance in response to variations in the balancing board 102. Additionally, the sensor 140, which may be a microphone, may capture the user 104's heartbeat rate or may capture the user 104's voice commands. It will be apparent to a person skilled in the art that location of the first set of sensors is not limited to the examples given above.

Additionally, one or more sensors from the first set of sensors may be installed at different locations in a room where the user 104 is operating the balancing board 102. For example, the sensor 144 may be installed on a wall 150, the sensor 146 may be installed on a wall 152, and the sensor 148 may be installed on a wall 154. These sensors also capture the user 104's reaction in response to variations in the balancing board 102. The sensors 144, 146, and 148 may, for example, include camera, depth sensors, and microphones. In an embodiment, the first set of sensors may be selectively activated or deactivated based on the balancing board level that is in operation.

The first set of sensors are further coupled, via wired or wireless arrangement, to a signal receiving arrangement (not shown in FIG. 1) included within the balancing board 102. The signal receiving arrangement may include one or more transceiver devices. The signal receiving arrangement receives one or more sensor signals from the first set of sensors. The one or more sensor signals are indicative of one or more reactions of the user 104 when he/she is operating the balancing board 102. The signal receiving arrangement may further be coupled, via wired or wireless arrangement, to the processor 118.

The first set of sensors may communicate the user reaction to the processor 118, via the signal receiving arrangement, based on which the processor 118 may automatically change balancing board level. Alternatively, the first set of sensors may directly communicate with the processor 118. For example, if user reaction sensed and captured by the first set of sensors indicate that the user 104 is easily able to maintain his/her balance while the Beginner level is in operation, the processor 118 may automatically and gradually increase the balancing board level to Easy, thereafter to Medium, and finally to Tough. On the contrary, the balancing board level may be decrease based on user reaction. For example, if heartbeat rate of the user 104 as captured by the sensor 140 exceeds a predefined safe rate, the balancing board level may be decreased or operation of the balancing board 102 may be automatically stopped. By way of another example, the user 104's face gestures, for example shock or awe, may also be used to automatically decrease balancing board level.

In an embodiment, balancing board levels may be changed in response to one or more of gesture and vocal commands received from the user 104. The sensor 140 may be a microphone, the sensors 144 and 146 may be cameras and the sensor 148 may be a depth sensor. These sensors alone or in combination may be used to capture the user 104's gesture and vocal commands.

The processor 118 may have pre-stored instructions regarding gesture or vocal commands. Alternatively, these instructions can be configured on the balancing board 102 by user 104. For example, a gesture command of "thumbs up" may be interpreted as "increase the balancing board level" command. Thus, when the user 104 makes "a thumbs up" gesture, the processor 118 may increase the balancing board level. Similarly, a gesture command of "thumbs down" may be interpreted as "decrease the balancing board level." Thus, when the user 104 makes "a thumbs down" gesture, the processor 118 may decrease the balancing board level. By way of another example, a gesture command of "touching nose" may be interpreted as "stop operation of the balancing board 102." In addition to gesture commands, voice commands of the user 104 may be used to change balancing board level. For example, the user 104 may shout out "BEGINNER" to activate the beginner level and similarly for other levels. By way of another example, the user 104 may shout out "START" to start operation of the balancing board 102 and the user 104 may shout out "STOP" to stop operation of the balancing board 102.

Balancing board level may also be changed automatically by the processor 116 after a predefined time period. For example, the balancing board level may be increased after every two minutes of operation. The user 104 may also change balancing board levels by using a mobile device 156. The mobile device 156 may include a balancing board software to control the balancing board 102. The mobile device 156 communicates the user 104's selection to the processor 118, based on which processor 118 changes the balancing board level. In an embodiment, the mode of operation of the balancing board 102 may be synchronized with the music playing on the mobile device 156. In another embodiment, a gyroscope or an accelerometer and a microphone installed in the mobile device 156 may be used to capture and sense the user 104's reaction.

In an embodiment, the processor 118 may use a speaker (not shown in FIG. 1) included in the balancing board 102 to indicate a change of balancing board level by outputting a predefined sound. For example, one beep may indicate change to an Easy level, two beeps may indicate change to a Medium level, and three beeps may indicate change to a Tough level. This may be helpful in mentally preparing the user 104 regarding change in the balancing board level.

In addition to the first set of sensors for use to sense and capture user reaction, the balancing board 102 includes a second set of sensors (not shown in FIG. 1) that are used to determine orientation, movement, and acceleration of the balancing board 102. Examples of the second set of sensors may include, but are not limited to, an accelerometer, a gyroscope, a microphone, a pressure sensor, a force sensor, a camera, a depth sensor for gesture recognition, a biometric sensor, a proximity sensor. The second set of sensors is coupled, via wired or wireless arrangement, to the signal receiving arrangement that receives one or more signals from the second set of sensors. The signal receiving arrangement is further coupled, via wired or wireless arrangement, to the processor 118.

The second set of sensors may be placed on body of the user 104, in the balancing board 102, or anywhere in the room used for operating the balancing board 104. For example, the balancing board 102 may have a pressure or force sensors placed below the first surface 106 to sense the pressure exerted by the user 104's feet on the first surface 106. By way of another example, the balancing board 102 includes a gyroscope or an accelerometer to determine orientation, movement, and acceleration of the balancing board 102. In an embodiment, a gyroscope or an accelerometer of the mobile device 156 may be used to determine this. The second set of sensors may communicate this data to the processor 118 via the sensor receiving arrangement. Alternatively, the second set of sensors may directly communicate this data to the processor 118.

Figure 2:
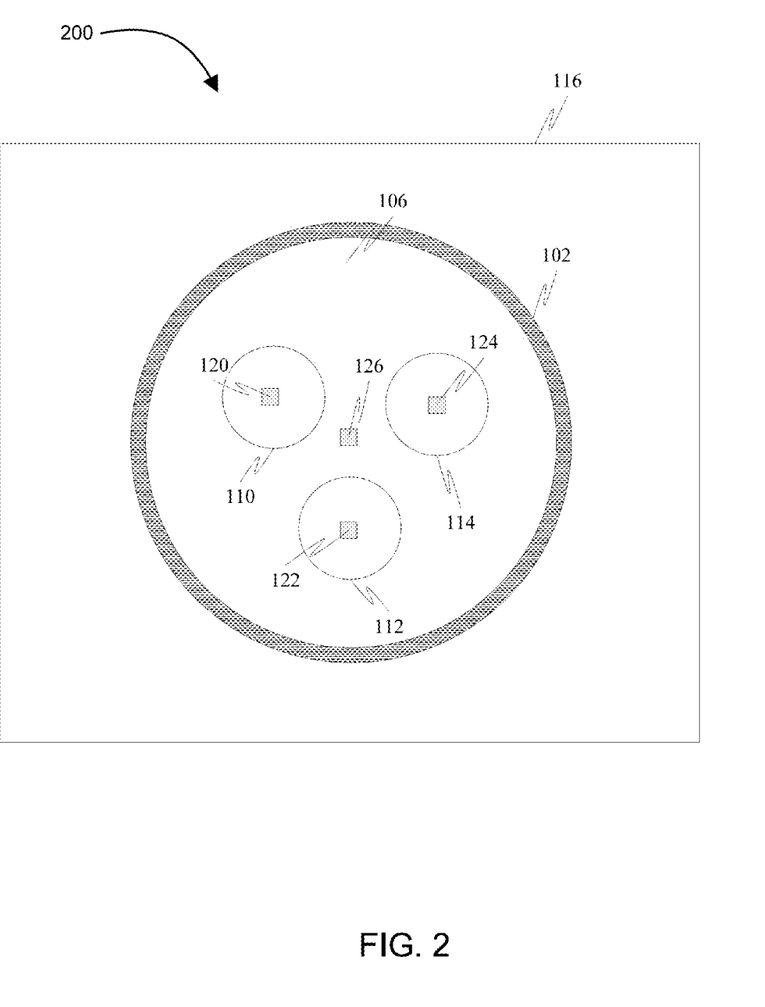
FIG. 2 illustrates a top view of a balancing board in accordance with an example embodiment.
Figure 3:
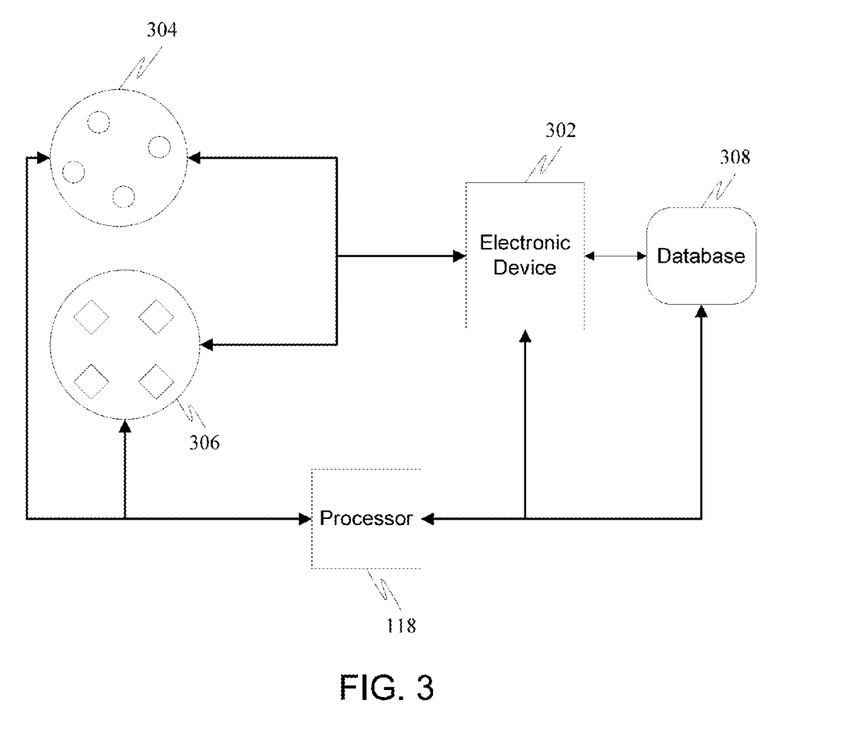
FIG. 3 illustrates communication between a balancing board and an electronic device, in accordance with an example embodiment.

A top view 200 of the example balancing board 102 is shown in FIG. 2, in accordance with an embodiment. Referring now to FIG. 3, communication between the balancing board 102 and an electronic device 302 is shown, in accordance with an embodiment. Examples of the electronic device 302 may include but are not limited to a mobile device (for example, mobile device 156), a computer, a Personal Digital Assistant (PDA), a Tablet, and a Laptop. The user reaction sensed and captured by a first set of sensors 304 and the data captured for the balancing board 102 by a second set of sensors 306 is communicated to the electronic device 302. It will be apparent to a person skilled in the art that the first set of sensors 304 and the second set of sensors 306 are the same as the first and second set of sensors disclosed in FIG. 1.

The first set of sensors 304 and the second set of sensors 306 may communicate the data to the processor 118 directly or via the signal receiving arrangement (not shown in FIG. 2). The processor 118 may further communicate this data to the electronic device 302. Alternatively, the first set of sensors 304 and the second set of sensors 306 may communicate this data to the electronic device 302 directly or via the signal receiving arrangement. The data may be communicated on wired or wireless arrangement, namely wireless communicating means, using various communication technologies. Examples of communication technologies for such wireless means may include but are not limited to Bluetooth, Microwave, WiFi, WiMAX, CDMA, GSM, GPRS, and infrared.

In an embodiment, the data sensed and captured by the first set of sensors 304 and the second set of sensors 306 may automatically be communicated to a server (not shown in FIG. 3), which may then upload this information on the Internet. For example, after completion of every balancing boarding level, the processor 118 may communicate the data to the server, which may then upload this information on social networking site, like Facebook and Google+. The user 104 may use this feature to compete with his/her peers on social networking sites.

After receiving this data, the electronic device 302 performs an analysis to determine a medical condition of the user 104. For example, it may be determined that the user has hypertension, cervical or lumbar spondylosis. The electronic device 302 may also store this data in a database 308. The analysis may be performed automatically by the electronic device 302 by comparing data captured for the user 104 with one or more of historic data for the user 104 stored in the database 308, the data captured for other users having similar demographic profile stored in the database 308, and benchmark data defined by medical personnel stored in the database 308. Alternatively, the data received from the processor 118 may be analyzed by medical personnel.

Based on the analysis performed and the medical condition determined for the user 104, the electronic device 302 may automatically design a training program for the user 104. The training program may include various combinations of balancing board levels. Thereafter, the electronic device 302 may communicate the designed training program to the processor 118. Alternatively, medical personnel may design a training program for the user 104 based on their analysis of the user 104's data. In an embodiment, the electronic device 302 may communicate the analysis to the processor 118. Thereafter, the processor 118 may design a training program for the user 104. After a training program has been designed, the processor 118 activates one or more mode of operations of the balancing board 102.

As an example of setting training programs for the user 104, based on the user 104's reaction captured by the first set of sensors 304 and the balancing board data captures by the second set of sensors 306, the electronic device 302 may determine that the user 104's reaction time is less than average. This may indicate a medical problem and thus the electronic device 302 may configure a training program such that, the user 104 starts with Beginner level of the balancing board 102 and gradually may progress to tougher balancing board levels. By way of another example, it may be determined that the user 104 is suffering from cervical spondylosis. Thus, the electronic device 302 may design a training program such that there are less jerky movements in the balancing board 102 while in operation.

Figure 4:
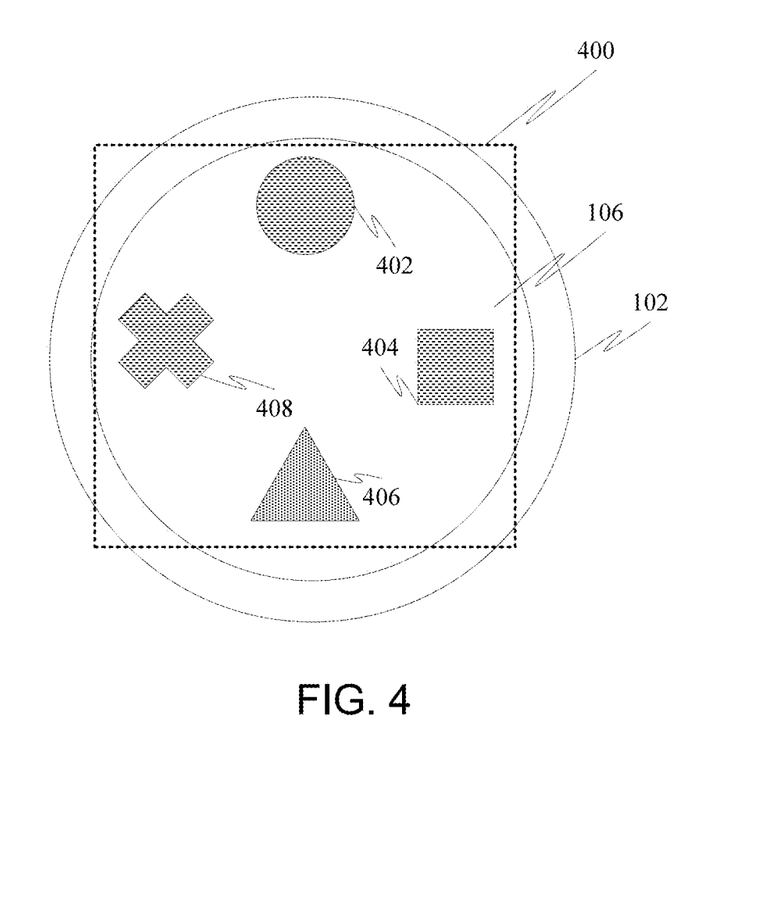
FIG. 4 illustrates a lighting pattern on a first surface of a balancing board, in accordance with an example embodiment.

To facilitate training of the user 104, who may be a first time user, the processor 118 activates a lighting pattern 400 (as shown in FIG. 4) on the first surface 106. The lighting pattern 400 comprises lighting one or more portions of the first surface 106; for example, the first surface 106 can be optionally implemented as a white surface, and an periphery of the second surface 108 is provided with a plurality of light sources, for example Light Emitting Diodes (LEDs), directed to illuminate the second surface 108 which then further reflects the light to provide an impressive light show onto the floor surface 116. In an embodiment, the first surface 106 may be made up of transparent or translucent material, for example, glass or plastics material. Beneath the first surface 106 are included a plurality of lighting means, for example, Light Emitting Diodes (LEDs), Organic LEDs (OLEDs), and Neon lights. The processor 118 may then selectively activate or deactivate one or more of the lighting means to render different illuminated shapes on the first surface 106. This is further explained in detail in conjunction with FIG. 4. The user 104 may thus be guided to step on illuminated portions on the first surface 106 so that the user 104 can be trained to operate the balancing board 102.

Referring now to FIG. 4, the lighting pattern 400 on the first surface 106 of the balancing board 102 is shown, in accordance with an exemplary embodiment. The lighting pattern 400 may include a circle pattern 402, a square pattern 404, a triangle pattern 406, and a cross pattern 408. The processor 118 may selectively illuminate one or more of these patterns to guide the user 104 regarding stepping on the first surface 106. Additionally, one or more of these patterns may be illuminated based on the current mode of operation of the balancing board 102 or a balancing board level activated by the processor 118. For example, when the Beginner level is in operation, the frequency of illuminating the one or more patterns may be less. However, when the Tough level is in operation, the frequency of illuminating the one or more patterns may be high.

In an embodiment, the shape of the illuminated pattern may be associated with the pressure that the user 104 needs to exert on the illuminated pattern of the first surface 106. For example, the circle pattern 402 may indicate that the user 104 needs to exert least amount of pressure on the circle pattern 402 on the first surface 106. By way of another example, the cross pattern 408 may be indicate that the user 104 needs to exert maximum amount of pressure on the cross pattern 408 on the first surface 106. Thus, using the methodology described above, the user 104 can be efficiently trained to operate the balancing board 102 by teaching the user 104 to exert the right amount of pressure on the first surface 106 for maintaining his/her balance while operating the balancing board 102.

Figure 5:
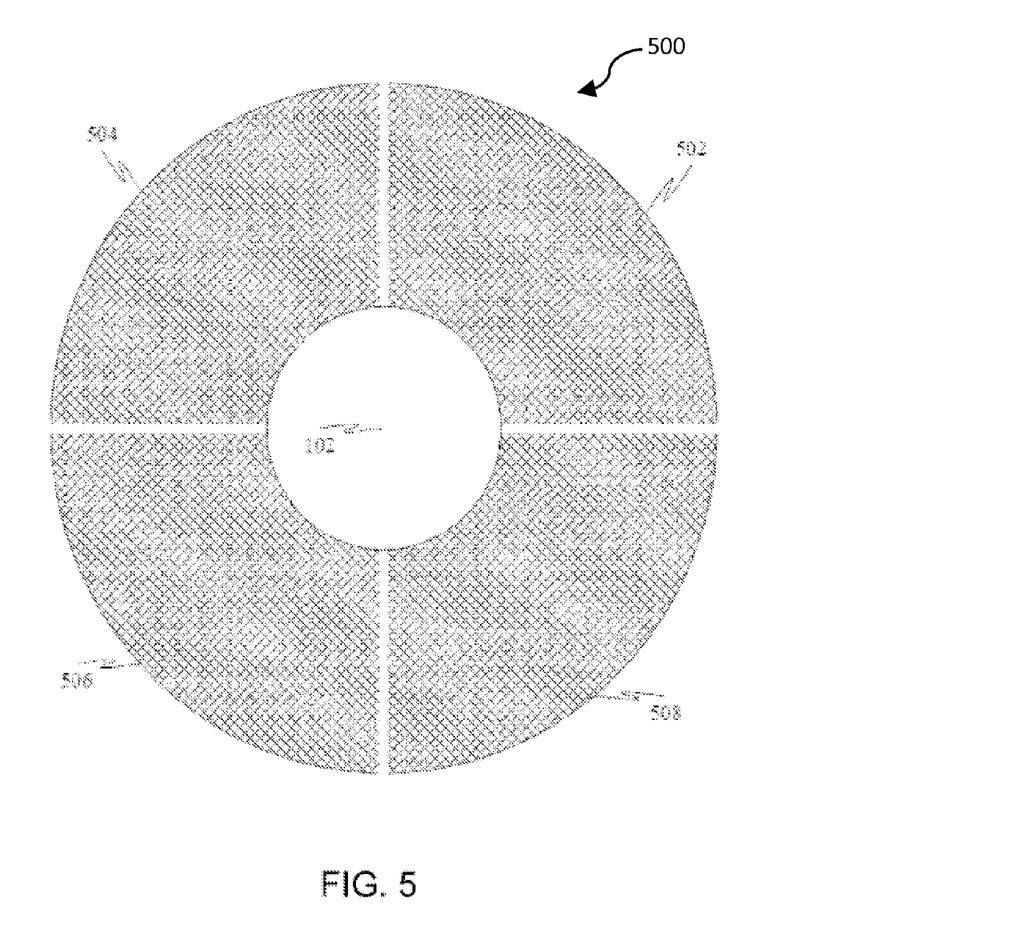
FIG. 5 illustrates a safety mechanism deployed by a balancing board, in accordance with an example embodiment.

In FIG. 5, there is illustrated a safety mechanism 500 deployed by the balancing board 102, in accordance with an example embodiment. The safety mechanism 500, for example, may include one or more airbags. While operating the balancing board 102, the user 104 may fall on the floor surface 116 and may potentially injure himself/hereself. To avoid such injuries, the balancing board 102 includes the safety mechanism 500, which may be deployed based on the user's 104 reaction sensed and captured by the first set of sensors. Additionally, the safety mechanism 500 may be deployed based on balancing board data captured by the second set of sensors.

The safety mechanism 500 may be deployed by the one or more actuators. For example, based on the user 104's reaction captured by the first set of sensors, the actuator 126 may ignite a gas generator propellant to rapidly inflate one or more airbags (for example, airbags 502, 504, 506, and 508) present in the balancing board 102, such that, the one or more airbags can be deployed on the floor surface 116. The one or more airbags may be deployed omni-directionally with respect to the balancing board 102 on the floor surface 116. In this case, for example, each of the airbags 502, 504, 506, and 508 may be deployed on the floor surface 116. Alternatively, in a more intelligent system, the one or more airbags may be deployed only in a particular region on the floor surface 116 based on the user 104's reaction. For example, based on the user 104's reaction, the area on which the user 104 may fall is determined and airbag 502 is accordingly deployed on the floor surface 116 to cushion the user 104's fall.

As an example of the method explained above, the sensor 142 attached to the user 104's head may be a proximity sensor and thus may determine the distance of the user 104's head from the floor surface 116. If this distance becomes less than a given threshold, the sensor 142 may trigger the actuator 126 via the signal receiving arrangement and/or the processor 118 to deploy the one or more airbags. By way of another example, the sensors 144, 146, and 148, which may be cameras and depth sensors which employ gesture recognition to predict that the user 104 might fall and thus trigger the actuator 126 via the processor 118 to deploy the one or more airbags. The sensors 144, 146, and 148 may also be able to determine the region on the floor surface 116 whereat the user 104 may fall. Thus, the sensors 144, 146, and 148 may trigger actuator 126 via the signal receiving arrangement and/or processor 118 to deploy one or more of the airbags 502, 504, 506, and 508.

Those skilled in the art will realize that the above recognized advantages and other advantages described herein are merely exemplary and are not meant to be a complete rendering of all of the advantages of the various embodiments.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A balancing board, comprising:
    a first surface for receiving one or more feet of a user when said balancing board is in operation;
    a second surface including one or more outwardly curved forms for engaging with a floor surface when said balancing board is in operation, wherein said second surface provides means for varying an orientation and movement of the balancing board relative to the floor surface;
    a signal receiving arrangement for receiving one or more sensor signals indicative of one or more user reactions when operating the balancing board in reaction to said variations in the orientation and movement of the balancing board, wherein the user is supported upon the first surface of the balancing board;
    a processor which is operable to receive said one or more sensor signals from a first set of sensors, comprising one or more sensors indicative of said one or more user reactions, wherein the processor is further operable to control means of changing a profile of the second surface;
    wherein said signal receiving arrangement is coupled to a second set of sensors, comprising one or more sensors and is operable to receive one or more signals from the second set of sensors, the second set of sensors being operable to determine an orientation, movement, and acceleration of the balancing board, and to communicate with the processor via the signal receiving arrangement; and
    one or more actuators, wherein the one or more sensors of the second set of sensors are coupled to the signal receiving arrangement and the processor and wherein the one or more sensors of the second set are operable to communicate with the one or more actuators, said actuators being operable to modify one or more outwardly curved forms of the balancing board.

2. The balancing board as claimed in claim 1, wherein the processor is operable to cause the balancing board to exhibit a plurality of levels.

3. The balancing board as claimed in claim 2, wherein each of the plurality of balancing board levels corresponds to a predefined combination of orientation, movement, and acceleration of the balancing board.

4. The balancing board as claimed in claim 2, wherein the processor is operable to automatically change between the balancing board levels based on the user feedback sensed by the first set of sensors.

5. The balancing board as claimed in claim 2, wherein the processor is operable to automatically advance from one of the plurality of balancing board levels to another of the plurality of balancing board levels after a predefined time period.

6. The balancing board as claimed in claim 1, wherein said signal receiving arrangement is coupled to the first set of sensors being, at least in part, attached in operation to a body of the user for sensing user reactions.

7. The balancing board as claimed in claim 6, wherein the balancing board is operable to communicate to an electronic device the user reaction sensed by the first set of sensors and the data sensed corresponding to the balancing board by the second set of sensors, wherein the electronic device is operable to perform analysis on the data received from the processor for determining a medical condition of the user.

8. The balancing board as claimed in claim 1, wherein the balancing board includes a safety mechanism which is deployable based on feedback sensed by the one or more sensors of the first set, the one or more sensors of the second set, or both, which sensors are coupled to the signal receiving arrangement, wherein said one or more actuators are operable to deploy the safety mechanism.

9. The balancing board as claimed in claim 8, wherein the safety mechanism comprises airbags.

10. The balancing board as claimed in claim 1, wherein said balancing board further includes means for moving the first surface relative to the second surface to facilitate a change in orientation and movement independently of any changes generated through the user balancing on the balancing board.

11. The balancing board as claimed in claim 1, wherein the one or more sensors of the second set of sensors comprises one or more of: an accelerometer, a gyroscope, a microphone, a pressure sensor, a force sensor, a camera, a depth sensor for gesture recognition, a biometric sensor, a proximity sensor.

12. The balancing board as claimed in claim 1, wherein the first surface is substantially planar in form.

13. The balancing board as claimed in claim 1, wherein the second surface of one or more outwardly curved forms is defined, at least in part, in profile by a volume of gas under pressure, wherein the volume of gas is inflated or deflated in operation based upon which mode of operation for the balancing board is activated by the processor, wherein the one or more actuators are operable to inflate or deflate the volume of gas to modify orientation and movement of the balancing board.

14. The balancing board as claimed in claim 1, wherein the one or more outwardly curved forms on the second surface are solid, wherein the one or more actuators are operable to selectively retract or extend the one or more curved forms to modify orientation and movement of the balancing board.

15. The balancing board as claimed in claim 1, wherein the first surface is operable to rotate independently about a substantially central axis of the balancing board, the first surface and the balancing board having the central axis common thereto, wherein the one or more actuators are operable to rotate the first surface.

16. The balancing board as claimed in claim 1, wherein the balancing board is operable to change balancing board levels in response to the user using a mobile device, wherein the mobile device is operable to communicate with the processor, the mobile device comprising a software to control the balancing board.

17. The balancing board as claimed in claim 1, wherein the balancing board is operable to change its balancing board level in response to one or more of gesture and vocal commands from the user, wherein the first or the second set of sensors is operable to sense and communicate one or more of gesture and vocal commands to the processor.

18. The balancing board as claimed in claim 1, wherein said balancing board is operable to communicate with an electronic device for configuring a balancing board training program for the user based on a performance analysis of the user, wherein the training program comprises a plurality of combinations of balancing board levels, therein the electronic device is operable to communicate the training program to the processor.

19. The balancing board as claimed in claim 1, wherein the balancing board is operable to be activated to present a lighting pattern on the first surface to facilitate training of the user, wherein the lighting pattern comprises lighting one or more portions of the first surface, the user stepping on the lighted one or more portions of the first surface for training.

* * * * *